(12) United States Patent
Sinelli

(10) Patent No.: US 6,443,016 B1
(45) Date of Patent: Sep. 3, 2002

(54) ELECTRIC CABLE ASSEMBLY WITH SACRIFICIAL CONDUCTORS

(76) Inventor: Robert Sinelli, 239 Cloverleaf Ct., Ann Arbor, MI (US) 48103

( * ) Notice: Subject to any disclaimer, the term of this patent is extended or adjusted under 35 U.S.C. 154(b) by 45 days.

(21) Appl. No.: 09/619,800

(22) Filed: Jul. 20, 2000

(51) Int. Cl.$^7$ ................................................ G01N 3/20
(52) U.S. Cl. ....................................................... 73/810
(58) Field of Search ........................... 73/808, 809, 810, 73/812, 813, 814, 815

(56) References Cited

U.S. PATENT DOCUMENTS

| | | | |
|---|---|---|---|
| 3,080,748 A | | 3/1963 | Burkley |
| 3,731,786 A | * | 5/1973 | Nagata et al. ................ 198/40 |
| 3,885,428 A | | 5/1975 | Dalferth |
| 3,958,455 A | | 5/1976 | Russell |
| 4,446,892 A | | 5/1984 | Maxwell |
| 4,498,282 A | | 2/1985 | Graetz |
| 4,812,831 A | * | 3/1989 | Laier ........................... 340/711 |
| 4,992,778 A | | 2/1991 | McKeen et al. |
| 5,172,730 A | | 12/1992 | Driver |
| 5,228,478 A | | 7/1993 | Kleisle |
| 5,690,146 A | | 11/1997 | Stammen |
| 5,834,942 A | * | 11/1998 | De Angelis ................... 73/158 |

* cited by examiner

Primary Examiner—Max Noori
(74) Attorney, Agent, or Firm—Harness, Dickey & Pierce, P.L.C.

(57) ABSTRACT

A cable assembly having a critical conductor and a sacrificial conductor and a critical conductor which has a fatigue life of a predetermined first length and the sacrificial conductor has a fatigue life of a predetermined second length shorter than the predetermined first length such that exposure of the cable assembly to repeated flexure or deteriorating substance causes the sacrificial conductor to fail before the critical conductor fails. Additionally, sacrificial conductors to be insulated with an insulation material less suited for the application so that the sacrificial conductors insulation will fail prior to the failure of the critical conductors. Positioning of sacrificial conductors around the circumference so failure from abrasion and chaffing will occur prior to critical conductors. A cable condition monitoring system for generating an alarm signal in response to the detection of a fault in the sacrificial conductors and a method for monitoring the condition of a cable assembly are also provided.

20 Claims, 3 Drawing Sheets

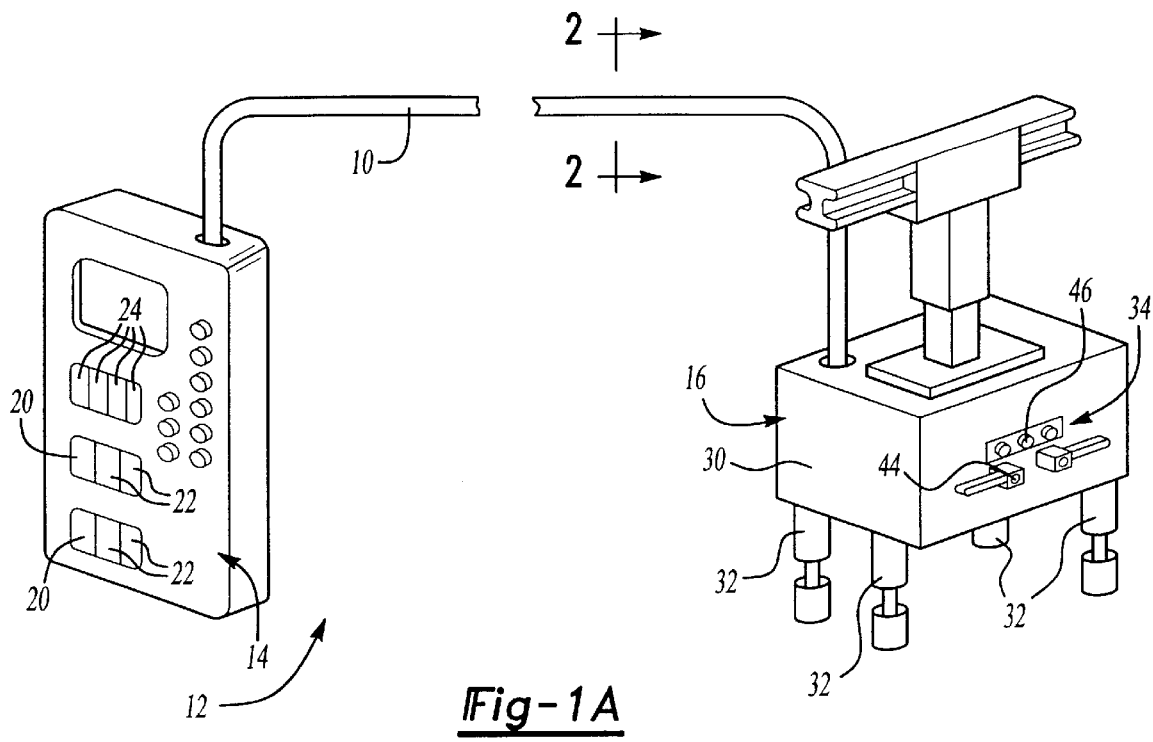
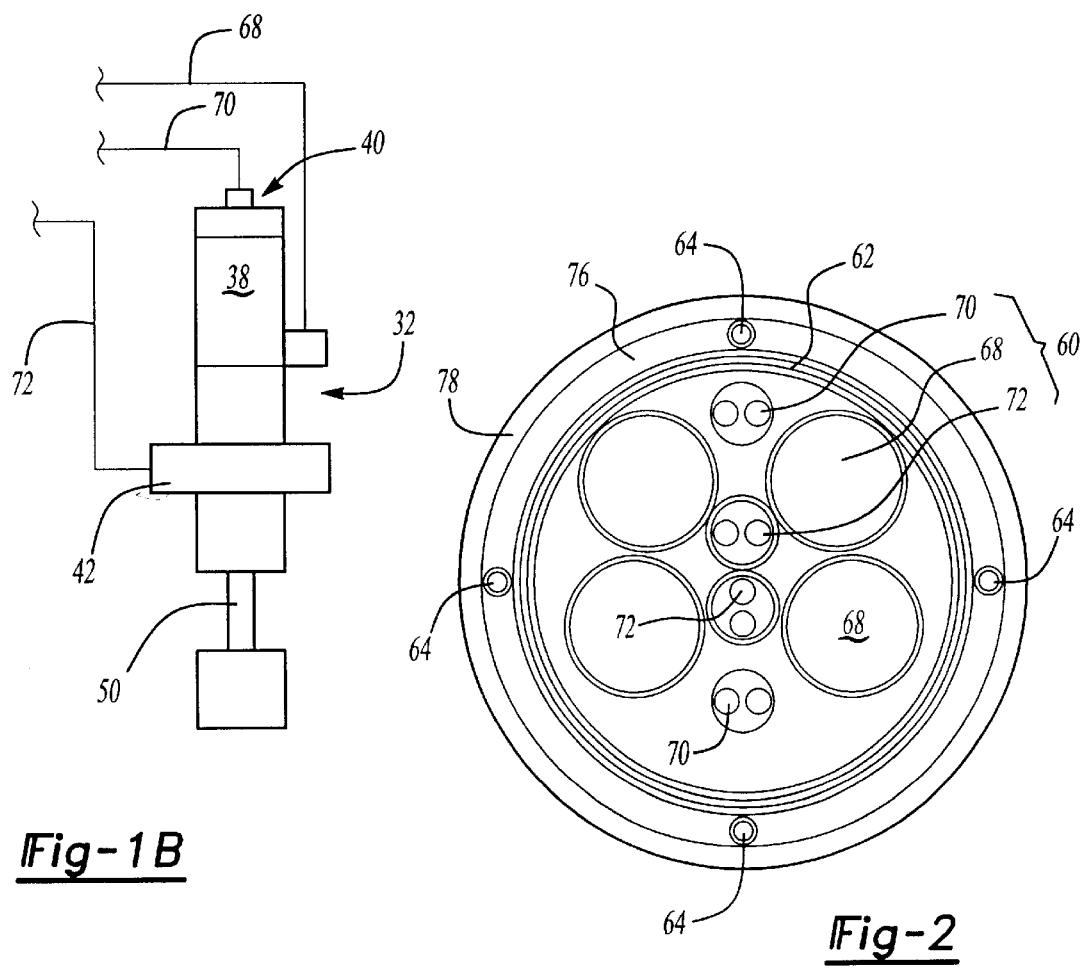
Fig-1A
Fig-1B
Fig-2

ELECTRIC CABLE ASSEMBLY WITH SACRIFICIAL CONDUCTORS

BACKGROUND OF THE INVENTION

1. Technical Field

The present invention relates generally to cable assemblies. More particularly, the present invention relates to a cable assembly whose condition is monitorable so that the cable assembly may be replaced prior to the failure of one or more critical conductors. The present invention also relates to a system and method for monitoring the condition of a cable assembly.

2. Discussion

Cable assemblies are commonly employed in industrial and telecommunications operations to transmit electrical power and/or signals between two devices. In situations where the two devices operate in stationary positions and are not exposed to environmental agents such as sunlight or chemicals that cause their insulating covers to degrade, the cable assembly will last indefinitely. However, where one device moves relative to the other, the cable assembly is susceptible to fatigue failures wherein one or more of the conductors that make up the cable assembly break due to repeated bending. Similarly, where the cable assembly is exposed to environmental agents which degrade the cable assembly's insulating material, the insulating material can fail causing the conductors that make up the cable assembly to come into electrical contact with one another or with an electrical ground.

Failures of these types are often catastrophic, completely disabling the devices to which they are coupled. Complicating matters is that these types of failures are typically difficult to predict and rather time consuming to repair. Repair may consist of the wholesale replacement of the cable assembly, or it may comprise the removal and replacement of one or more areas that are suspected of being damaged.

To combat down-time associated with failures in cable assemblies, some users of cable assemblies simply incorporate additional (spare) conductors into the cable assembly which are then be used to replace one of the actively used conductors upon the occurrence of a fault. This solution, however, has several drawbacks. One drawback relates to fact that the additional cables can be relatively expensive and as such, the incorporation of spare cables further increase the cost of the cable assembly. Another drawback relates to the ease with which the additional cables are festooned between the devices and the impact of additional cable weight on the person or mechanism that must position the device or devices that are coupled to the cable assembly. Yet another drawback concerns the occurrence of a failure related down-time. Failures in an active conductor will still result in some down-time, albeit a smaller amount of down-time than had the cable assembly not included a spare.

Another approach has been to predict a lifespan of the cable assembly and simply replace the cable assembly after it has been in use for a duration equal its lifespan, regardless of its actual condition. This approach, however, has not been completely successful due difficulties in calculating the lifespan of the cable assembly. Furthermore, this approach is rather costly, as cable assemblies are replaced regardless of their actual condition.

SUMMARY OF THE INVENTION

It is one object of the present invention to provide a cable assembly which may be readily monitored so that its condition can be determined prior to the failure of a conductor which is necessary for the operation of the devices to which the cable assembly is connected.

It is another object of the present invention to provide a cable assembly having a sacrificial conductor which permits the condition of the cable assembly to be monitored.

It is a further object of the present invention to provide a cable condition monitoring system for generating an alarm signal in response to the detection of a fault in a sacrificial conductors in the cable assembly.

It is yet another object of the present invention to provide a method for monitoring the condition of a cable assembly.

In one preferred form, the present invention provides a cable assembly having a critical conductor and a sacrificial conductor. The critical conductor has a fatigue life of a predetermined first length and the sacrificial conductor has a fatigue life of a predetermined second length which is shorter than the predetermined first length such that exposure of the cable assembly to repeated flexure causes the sacrificial conductor to fail before the critical conductor fails. A cable condition monitoring system for generating an alarm signal in response to the detection of a fault in the sacrificial conductors and a method for monitoring the condition of a cable assembly are also provided.

BRIEF DESCRIPTION OF THE DRAWINGS

Additional advantages and features of the present invention will become apparent from the subsequent description and the appended claims, taken in conjunction with the accompanying drawings wherein:

FIG. 1A is a perspective view of a cable assembly constructed in accordance with a preferred embodiment of the present invention, the cable assembly being shown in operative association with automated fastening device;

FIG. 1B is an enlarged side elevational view of a portion of the automated fastening device of FIG. 1A;

FIG. 2 is a cross-sectional view of the cable assembly taken along the line 2—2 of FIG. 1A;

DETAILED DESCRIPTION OF THE PREFERRED EMBODIMENT

Figure 3:
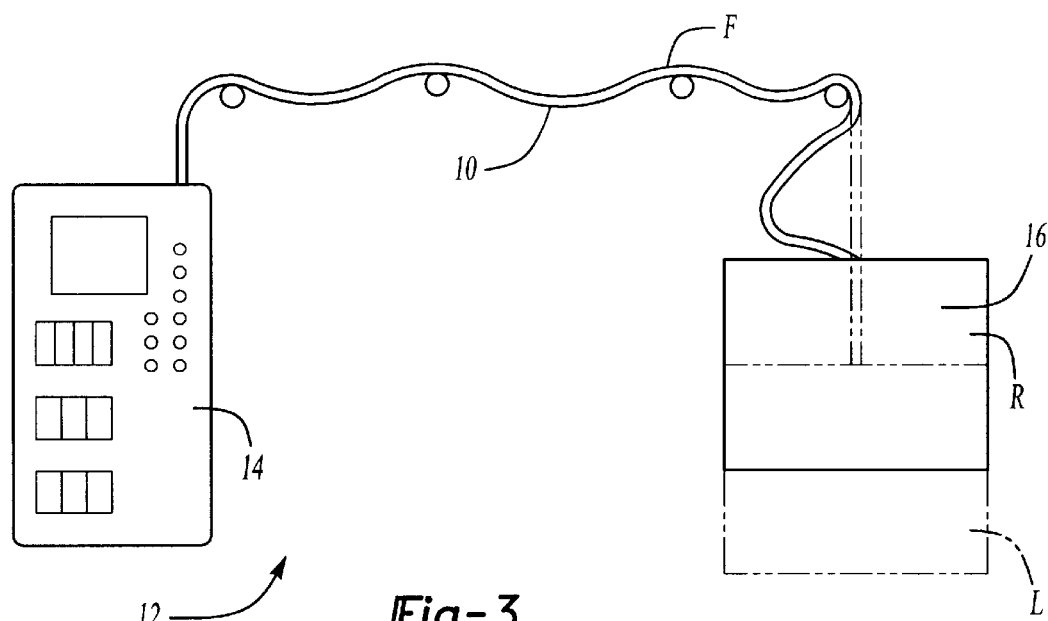
FIG. 3 is a schematic illustration of the automated fastening device of FIG. 1A, showing the cable assembly at various times during the operation of the automated fastening device.

With reference to FIGS. 1A and 1B of the drawings, a cable assembly constructed in accordance with the teachings of the present invention is generally indicated by reference numeral 10. Cable assembly 10 is shown in operative association with an automated fastening device 12. Automated fastening device 12 conventionally includes a control panel 14 and a tool assembly 16. Control panel 14 conventionally includes a plurality of power amplifiers 20, a plurality of servo power supplies 22 and plurality of spindle modules 24. Tool assembly 16 conventionally includes a tool structure 30, a plurality of spindle assemblies 32 and a subpanel 34 for remotely controlling tool assembly 16. In the example provided, each of the spindle assemblies 32 includes a motor assembly 38 having a DC or AC electric motor and a gearbox, a resolver 40 and a torque transducer 42. Subpanel 34 conventionally includes a plurality of control buttons 44 which permit a technician to remotely operate tool assembly 16 and a plurality of status lights 46 for indicating the status of a fastening operation.

Cable assembly 10 electrically couples control panel 14 and tool assembly 16, providing a means for powering tool assembly 16 as well as for transmitting fastening data to spindle modules 24. The operation of automated fastening device 12 is beyond the scope of this invention and as such, need not be discussed in detail. Briefly, actuation of the control buttons 44 causes power amplifiers 20 and servo power supplies 22 to cooperatively supply electrical power to their associated motor assemblies 38. Each resolver 40 is operable for monitoring the rotational position of the rotor of its respective motor assembly 38 and generating a resolver signal in response thereto. The resolver signal is received by an associated one of the spindle modules 24 and an associated one of the servo power supplies 22. Spindle modules 24 employ the resolver signals to monitor the angle through which an output spindle 50 of their respective motor assembly 38 has rotated. Servo power supplies 22 employ the resolver signals to control the switching of electrical power to their respective motor assembly 38 to change the magnetic field produced by the stator of the motor assembly 38 so that the rotor may rotate properly.

Tightening of a fastener generates a torque reaction that is transmitted through spindle assembly 32 to torque transducer 42. Torque transducer 42 produces a transducer signal that is proportional to the corresponding torque reaction that is applied against it. Spindle modules 24 employ the transducer signal to monitor the torque that is output from their respective spindle assembly 32.

With reference to FIG. 2, cable assembly 10 is shown to include a plurality of critical conductors 60, a conductive shield 62 and a plurality of sacrificial conductors 64. In the particular embodiment illustrated, the plurality of critical conductors 60 includes a plurality of power cables 68, a plurality of resolver cables 70 and a plurality of transducer cables 72. Each of the power cables 68 electrically couples a motor assembly to an associated one of the servo power supplies 22. Each of the resolver cables 70 electronically couples a resolver to an associated one of the spindle modules 24 and an associated one of the servo power supplies 22. Each one of the transducer cables 72 electronically couples one of the torque transducers 42 with an associated one of the spindle modules 24. Conductive shield 62 encircles the plurality of critical conductors 60 and conventionally inhibits the transmission of electrical noise therethrough. Each of the plurality of sacrificial conductors 64 is formed from an appropriate wire (e.g., 20 ga. insulated solid copper wire) and disposed in a filler material 76. The plurality of sacrificial conductors 64 are circumferentially spaced about conductive shield 62. An outer jacket 78, formed from an appropriate insulating material such as polyurethane or polyvinyl chloride encircles the plurality of sacrificial 110 conductors 64 and filler material 76.

A failure in a critical conductor 60 will likely interrupt the transmission of electrical power, the resolver signal or the transducer signal between tool assembly 16 and control panel 14, thus preventing the associated spindle assembly 32 from operating. In modern high-volume assembly processes where production rates can be greater than 60 pieces per hour, interruptions of these types essentially render tool assembly 16 inoperative, even when only one spindle assembly 32 is effected.

A major cause of failures in the critical conductors 60 stems from fatigue that results from the repeated operation of tool assembly 16. In FIG. 3, cable assembly 10 is schematically shown festooned (i.e., supported at several intervals) between control panel 14 and tool assembly 16. When tool assembly 16 is not in use it is maintained in a raised condition as designated by reference letter "R" so as to be out of the way of the assembly technicians. When tool assembly 16 is operated, it is lowered onto a component as indicated by reference letter "L" and spindle assemblies 32 are activated. Raising and lowering of tool assembly 16 causes section designated by reference letter "F" of cable assembly 10 to bend. The repeated bending of section F during the operation of tool assembly 16 work hardens the electrical wires that make up the conductors (i.e., critical conductors 60 and sacrificial conductors 64) in cable assembly 10. Eventually, one or more of the conductors in cable assembly 10 will fatigue and break, causing an interruption, which could disable tool assembly 16 if the conductor is one of the critical conductors 60.

To avoid failures in the critical conductors 60 which would disable tool assembly 16, sacrificial conductors 64 are monitored, either continuously or periodically, to predict the occurrence of a catastrophic failure in the critical conductors 60. Sacrificial conductors 64 are selected to have a predetermined fatigue life that is shorter in duration than the fatigue life of any of the critical conductors 60. Sacrificial conductors 64 are preferably incorporated into cable assembly 10 such that they are exposed to relatively higher levels of strain during the operation of tool assembly 16 than any of the critical conductors 60. Configuration in this manner ensures that one or more of the sacrificial conductors 64 will fail from fatigue prior to the failure of a critical conductor 60. Accordingly, monitoring of the condition of the sacrificial conductors 64 permits a failure of a sacrificial conductor 64 to be noted well before a fatigue failure of one of the critical conductors 60. This permits cable assembly 10 to be serviced (e.g., replaced) at a time which is convenient and which does not impact the productive use of tool assembly 16.

Figure 4:
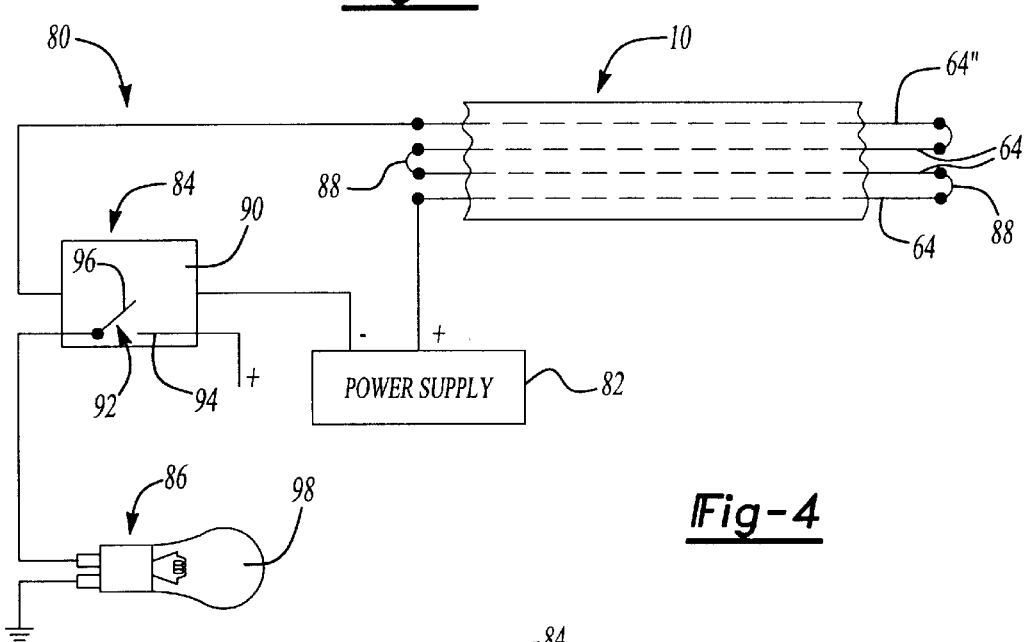
FIG. 4 is a schematic illustration of a portion of the automated fastening device illustrating the system for monitoring the condition of a cable assembly.

In FIG. 4 a fault detection device 80 for monitoring the condition of the sacrificial conductors 64 is schematically illustrated to include a power supply 82, a fault monitor 84 and an alarm device 86. Power supply 82 is operable for providing a predetermined electrical signal to the plurality of sacrificial conductors 64. Fault monitor 84 monitors the transmission of the electrical signal through the sacrificial conductors 64 and responsively generates an alarm signal in response to the detection of a fault. In the particular embodiment illustrated, power supply 82 is operable for providing an electrical signal having a continuous direct current voltage which is transmitted to a first end of sacrificial conductor 64'. The sacrificial conductors 64 are coupled together in series through a plurality of electrical jumpers 88, thereby creating a continuous electrical path through which electrical signal travels. Sacrificial conductor 64" is coupled to fault monitor 84, which is illustrated to be a control relay or solid state device 90 having a switching element 92.

A first leg 94 of switching element 92 is electrically coupled to a source of power (not specifically shown) and a second leg 96 of switching element 92 is coupled to one electrical terminal of alarm device 86. While alarm device 86 is illustrated to be an indicator light 98, those skilled in the art will understand that alarm device 86 may also or alternatively include an audio alarm device or a digital output which is received by a programmable logic controller or a computer which generates an appropriate predetermined response, including the generation of an e-mail message.

Figure 5:
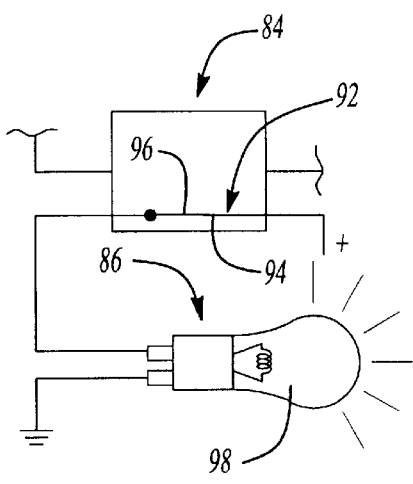
FIG. 5 is a schematic illustration similar to that of FIG. 4 but illustrating the system after a defect has been detected.

Control relay 90 is configured such that upon receipt of the electric signal that is transmitted through the sacrificial conductors 64, switching element 92 is positioned into an open condition as shown in FIG. 4. When one of the sacrificial conductors 64 succumbs to fatigue and breaks, however, switching element 92 reverts to its normal condition open, closed or both, closed being shown in FIG. 5, generating an alarm signal which is transmitted to alarm device 86 so that a predetermined alarm indicative of the need to preventatively service cable assembly 10 is generated. In the particular embodiment illustrated, the predetermined alarm is the illumination of indicator light 98.

Figure 6:
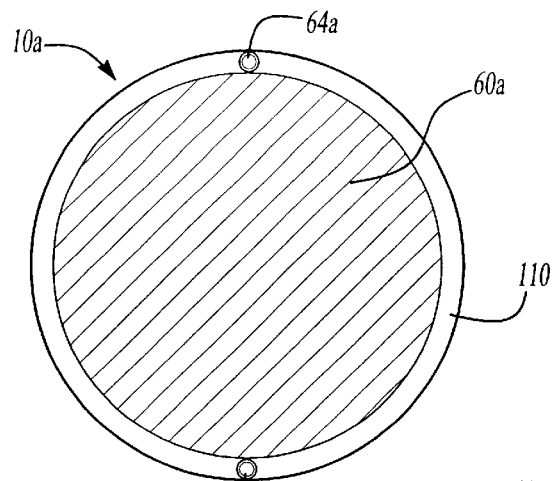
FIG. 6 is a cross-sectional view similar to FIG. 2 but illustrating a second embodiment of the present invention.

In FIG. 6, a cable assembly constructed in accordance with a second embodiment of the present invention is generally indicated by reference numeral 10a. Cable assembly 10a is shown to include a single critical conductor 60a and two sacrificial conductors 64a. Critical conductor 60a is shown to be a relatively large cable having an appropriate insulating material 110 which encircles it. Sacrificial conductor 64a includes a relatively small cable and a separate insulating material. Sacrificial conductor 64a is disposed within insulating material 110. Configuration of cable assembly 10a in this manner is particularly well adapted for welding applications, such as in automated spot resistance welding tools where a relatively large amount of electrical power is transmitted through critical conductor 60a.

Figure 7:
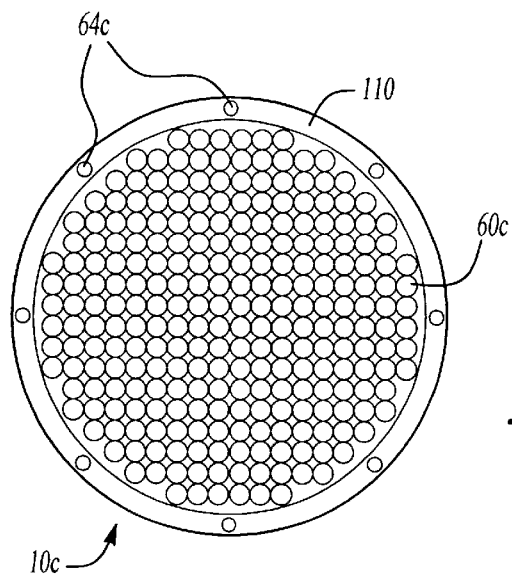
FIG. 7 is a cross-sectional view similar to FIG. 2 but illustrating a third embodiment of the present invention.

The embodiment illustrated in FIG. 7 is similar to that of FIG. 6, except that cable assembly 10c is shown to include several sacrificial conductors 64c that are disposed within insulating material 110 and circumferentially spaced about critical conductor 60c. In this embodiment, the cable assembly 10c, is shown to include a plurality of sacrificial conductors 64c that are disposed radially outward of the plurality of critical conductor 60c. This embodiment provides for failure of sacrificial conductors due to flexing fatigue, environmental fatigue, exposure to chemicals and abrasion or chaffing that could be caused from use in a cable track.

FIG. 7 could also be viewed as a cross section of an individual conductor, such as used in aircraft. The critical conductor is made up of many smaller non-insulated conductors bundled together to create one large conductor. For this embodiment the sacrificial conductors should be sized appropriately so as to allow them to fail when the insulation in which they are disposed is breached or chaffed (i.e. rubbing on the airframe). A common cause is vibration and +and −"G" loads associated with takeoff and landing, turbulence and maneuvering.

Figure 8:
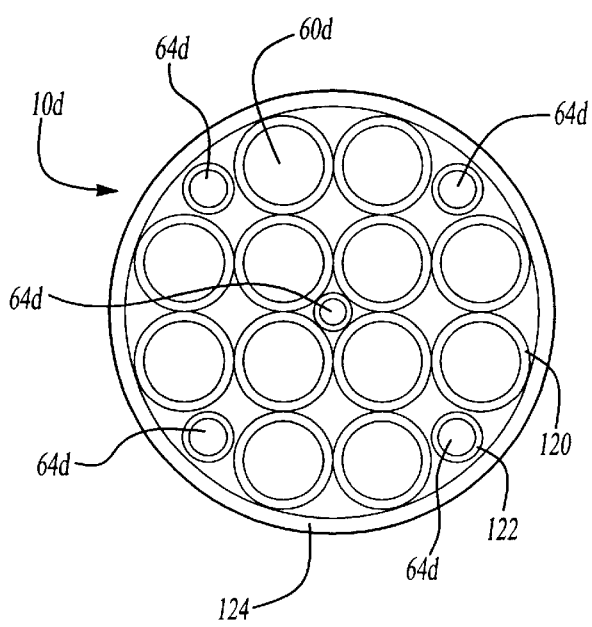
FIG. 8 is a cross-sectional view similar to FIG. 2 but illustrating a fourth embodiment of the present invention.

The embodiment illustrated in FIG. 8 shows cable assembly 10d to include twelve critical conductors 60d and five sacrificial conductors 64d. Each of the critical conductors 60d is shown to include a first insulation 120, which is highly resistant to an insulation damaging substance, such as a contaminant, to which cable assembly 10d will be exposed during its use. Each of the sacrificial conductors 64d is shown to have a second insulation 122, which is less resistant to the insulation damaging substance. In the particular embodiment illustrated, the insulation damaging substance is oil, first insulation 120 is polyurethane and second insulation 122 is polyvinyl chloride. The critical conductors 60d and sacrificial conductors 64d are encircled with an insulating material 124, preferably the material which forms the first insulation 120.

Configuration of cable assembly 10d in this manner creates a barrier (i.e., insulating material 124) which prevents the critical conductors 60d and sacrificial conductors 64d from being exposed to oil. Prolonged exposure to oil will eventually cause insulating material 124 to fail, thereby exposing the critical conductors 60d and sacrificial conductors 64d to oil. As sacrificial conductors 64d are insulated with a material that is less resistant to oil than the material which is employed to insulate the critical conductors 60d, the second insulation 122 will fail prior to the first insulation 120. Accordingly, continuous or periodic monitoring of sacrificial conductors 64d will detect faults wherein one or more of the sacrificial conductors 64d is conducting the electric signal to an electrical ground, or causing a physical failure of the sacrificial conductor or a change in impedance or capacitance or other change in measurable quality.

Accordingly, monitoring of the condition of the sacrificial conductors 64d permits a failure of a second insulation 122 to be noted well before a failure of the first insulation 120 on one of the critical conductors 60d. This permits cable assembly 10d to be serviced prior to a failure in the first insulation 120 which causes a critical conductor 60d to conduct electric current to an electrical ground, or other critical conductors or sacrificial conductors. As mentioned above, monitoring of the condition of the sacrificial conductors 64d permits cable assembly 10d to be serviced at a time which is convenient and which does not impact the productive use of tool assembly 16.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A cable assembly for electrically connecting a first device to a second device, the cable assembly comprising:

at least one critical conductor, the at least one critical conductor having a predetermined first fatigue life and being configured to be electrically coupled to the first and second devices; and at least one sacrificial conductor formed from material that hardens on exposure to repeated bending, the at least on sacrificial conductor having a predetermined second fatigue life, that is shorter than the predetermined first fatigue life such that exposure of the cable assembly to repeated flexure causes the at least one sacrificial conductor to fail before the at least one critical conductor.

2. The cable assembly of claim 1, wherein the at least one critical conductor is insulated with a first insulator and the at least one sacrificial conductor is insulated with a second insulator, the first insulator being relatively more resistant to contaminants than the second insulator such that prolonged exposure to contaminants will breach the second insulator before the first insulator is breached.

3. The cable assembly of claim 2, wherein a contaminant resistant insulator surrounds the at least one critical conductor and the at least one sacrificial conductor.

4. The cable assembly of claim 2, wherein the first insulator is best suited for the application and the second insulator is less suited for the application.

5. The cable assembly of claim 1, wherein the at least one sacrificial conductor is formed from a material or alloy that will fatigue and fail sooner than the at least one critical conductor.

6. The cable assembly of claim 1, wherein the at least one sacrificial conductor is formed to an appropriate diameter so it will fatigue and fail sooner than the at least one critical conductor.

7. The cable assembly of claim 1, wherein the at least one sacrificial conductor is positioned in the cable assembly such that it is exposed to a relatively higher level of strain than the at least one critical conductor.

8. The cable assembly of claim 1, wherein a plurality of the sacrificial conductors are spaced circumferentially about the at least one critical conductor.

9. The cable assembly of claim 8 wherein the plurality of sacrificial conductors are spaced circumferentially about the at least one critical conductor so that at least one sacrificial conductor will fail due to chaffing, abrasion, rubbing or the like, prior to exposure or failure of the at least one critical conductor.

10. The cable assembly of claim 8, wherein the plurality of sacrificial conductors are disposed in a common insulating member.

11. The cable assembly of claim 8, wherein the plurality of sacrificial conductors are coupled together in series.

12. The cable assembly of claim 1, wherein the at least critical conductor includes at least one of a power cable, a signal cable and a data cable.

13. The cable assembly of claim 1, further comprising a conductive shield member disposed between the at least one critical conductor and the at least one sacrificial conductor.

14. A cable condition monitoring system comprising:
a cable assembly having at least one critical conductor and at least one sacrificial conductor, the at least one critical conductor having a first predetermined fatigue life and being configured to electrically couple a first device to a second device, the at least one sacrificial conductor being formed from a material that hardens on exposure to repeated bending, the at least one sacrificial conductor having a second predetermined fatigue life, that is shorter than the first predetermined fatigue life such that exposure of the cable assembly to repeated flexure causes the at least one sacrificial conductor to fail before the at least one critical conductor; and
a fault detection device operative connected to the at least one sacrificial conductor such that failure of the at least one sacrificial conductor provides a signal in response to the failure of said at least one sacrificial conductor.

15. The cable condition monitoring system of claim 14, wherein the fault is a lack of electrical continuity in the at least one sacrificial conductor.

16. The cable condition monitoring system of claim 14, wherein the fault is electrical continuity between the at least one sacrificial conductor and an electrical ground or conductive shield.

17. The cable condition monitoring system of claim 14, wherein the fault monitor is an electrical relay or solid state device.

18. The cable condition monitoring system of claim 17, wherein the electrical relay or solid state device is a normally closed relay or normally open relay.

19. A method for monitoring a condition of a cable assembly, the method comprising the steps of:
providing a cable assembly having at least one critical conductor and at least one sacrificial conductor, the at least one critical conductor being configured to electrically couple a first device to a second device and having a predetermined first fatigue life, the at least one sacrificial conductor being formed of a material that hardens on exposure to repeated bending, the at least one sacrificial conductor having a predetermined second fatigue life, that is shorter than the predetermined first fatigue life;
providing an electrical signal to a first end of said at least one sacrificial conductor;
monitoring the electrical signal at a second end of said at least one sacrificial conductor and responsively detecting a fault condition.

20. The method of claim 19, wherein the electrical signal is selected from a group of electrical signals consisting of a voltage of a predetermined magnitude, a voltage of a predetermined frequency, a predetermined inductance, a predetermined capacitance and a predetermined resistance.

* * * * *

UNITED STATES PATENT AND TRADEMARK OFFICE
CERTIFICATE OF CORRECTION

PATENT NO.   : 6,443,016 B1
DATED        : September 3, 2002
INVENTOR(S)  : Robert Sinelli It is certified that error appears in the above-identified patent and that said Letters Patent is hereby corrected as shown below:

<u>Column 6,</u>
Line 55, "on" should be -- one --.

<u>Column 8,</u>
Line 1, after "life" please delete ",".
Line 6, "operative" should be -- operatively --.
Line 9, "said" should be -- the --.
Lines 33 through 34, "that is shorter than the predetermined first fatigue life" should be -- the predetermined second fatigue life being shorter than the predetermined first fatigue life --.
Line 35, "said" should be -- the --.
Line 37, "said" should be -- the --.

Signed and Sealed this

Twenty-fifth Day of February, 2003

JAMES E. ROGAN
*Director of the United States Patent and Trademark Office*